United States Patent [19]

Pezzi

[11] 4,403,501
[45] Sep. 13, 1983

[54] METHOD AND DEVICE FOR THE ELECTROPNEUMATIC TESTING OF CIGARETTE FILTERS

[75] Inventor: Giovanni Pezzi, Bologna, Italy

[73] Assignee: Cir S.p.A. Divisione Sasib, Bologna, Italy

[21] Appl. No.: 228,881

[22] Filed: Jan. 22, 1981

[30] Foreign Application Priority Data

Feb. 5, 1980 [IT] Italy .............................. 12433 A/80

[51] Int. Cl.³ ............................................. G01N 15/08
[52] U.S. Cl. ........................................ 73/38; 73/45.2
[58] Field of Search ................. 73/38, 45, 45.1, 45.2; 209/535, 537, 591

[56] References Cited

U.S. PATENT DOCUMENTS

| | | |
|---|---|---|
| 3,412,856 | 11/1968 | Esenwein. |
| 3,690,149 | 9/1972 | Pezzi ........................................ 73/38 |
| 4,120,194 | 10/1978 | Reuland ................................ 73/45.2 |
| 4,223,551 | 9/1980 | Greve et al. ............................. 73/38 |
| 4,227,397 | 10/1980 | Neri ......................................... 73/38 |
| 4,287,754 | 9/1981 | Heitmann et al. ...................... 73/38 |
| 4,325,250 | 4/1982 | Bolt et al. ................................ 73/38 |

Primary Examiner—Steven L. Stephan
Assistant Examiner—Joseph W. Roskos
Attorney, Agent, or Firm—Spencer & Kaye

[57] ABSTRACT

A method and device for the electropneumatic testing of the air permeability of filter plugs for filter cigarettes. At one end of the filter plug there is applied a pneumatic pressure, the other end of the filter cigarette being connected, through a bore with the atmosphere. The pneumatic pressure applied at the inlet end of the cigarette plug is transformed into an electric test signal, and the signal is compared with an upper alarm threshold and with a higher upper reject threshold respectively, as well as with a lower alarm threshold and an inferior lower reject threshold. The test signal emitted upon reaching of the upper or lower alarm threshold initiates the operation of alarm indicators and/or sends a signal for the control of the filter plug producing machine, so as to modify the air permeability of the filter plugs. Upon reaching the upper or lower reject threshold, it causes rejection of the defective filter plugs.

14 Claims, 2 Drawing Figures

METHOD AND DEVICE FOR THE ELECTROPNEUMATIC TESTING OF CIGARETTE FILTERS

SUMMARY OF THE INVENTION

The invention relates to the filter rods used in filter tip cigarette production.

One of the essential parameters of the above filter rods in their permeability to the air, because both the filtering effect and the facility with which the smoke is drawn by the smoker depend on it.

The invention is aimed at ensuring the homogeneity of production of the filter rods, thus ensuring that their permeability to the air is included between two preset thresholds, one higher and the other lower.

For this purpose, the invention relates to a method for inspecting the permeability to the air of the filter rods intended for the production of filter tip cigarettes, or the like. This method is characterized by the fact that a pneumatic pressure is applied to one end of the filter rod, while the other end of the filter rod is caused to communicate with the atmosphere through a calibrated passage hole and the pneumatic pressure reached at the inlet into the filter rod is converted into an electric inspection signal which is compared with two reject thresholds, one higher and the other lower, thus giving rise to an electric reject signal which causes the filter rod to be rejected if its permeability to the air exceeds the higher reject threshold or does not reach the lower reject threshold.

According to a further feature of the invention, the electric inspection signal is compared also with two alarm thresholds, one higher and the other lower, contained in the band included between the two reject signals and closest to the desired value of the permeability to the air of the filter rods, thus giving rise to an electric alarm signal which actuates an optical and/or acoustic indicator, and, for instance, causes the lighting of LED diodes, when the permeability to the air of the filter rod exceeds the higher alarm threshold (without reaching yet the higher reject threshold) or does not reach the lower alarm threshold (even if the lower reject threshold has already been exceeded). On the basis of this alarm signal and to the indication caused by it, the operator may correct the permeability to the air of the filter rods on the filter making machine.

According to another feature of the invention, the electric alarm signal is used, by means of appropriate electric circuits, for controlling the filter rod making machine in such a way as to automatically correct the permeability to the air of the finished filter rods.

The four thresholds can be individually corrected by a single associated level adjusting means. Preferably, the possibility is also provided to change simultaneously all the four thresholds by a preset percentage value with respect to the preset reject and alarm values.

BRIEF DESCRIPTION OF THE DRAWINGS

These and other features of the invention and the resulting advantages will be understood from the following description of a preferred embodiment illustrated as an example in the attached drawings, in which.

DESCRIPTION OF THE PREFERRED EMBODIMENTS

Figure 2:
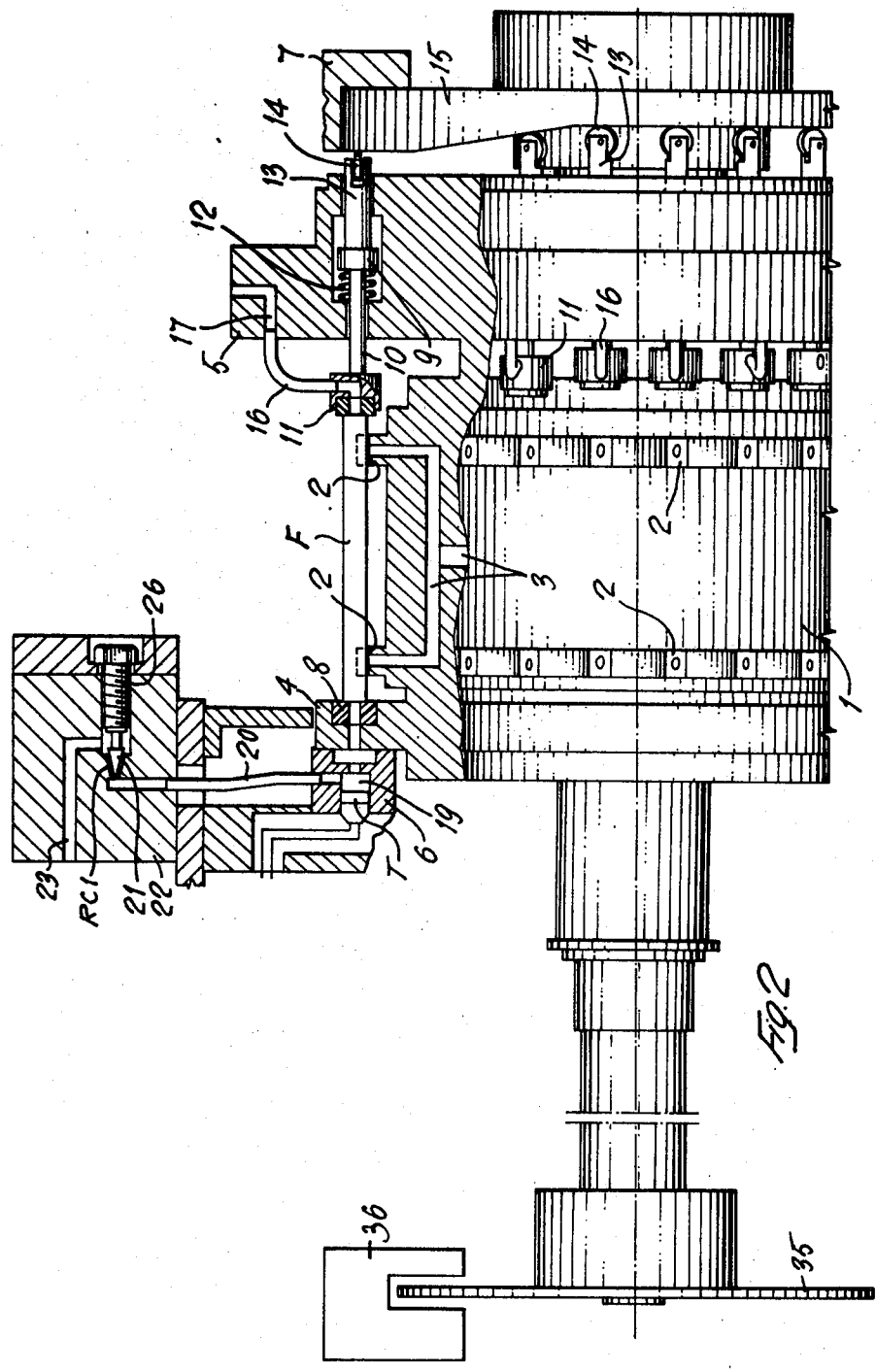
FIG. 2 shows a side elevation with parts in section of the mechanical part of a device according to the invention.

The method according to the invention can be carried out—as an example—by means of the mechanical device shown in FIG. 2. This device consists of a continuously or intermittently rotating drum 1 provided peripherally with a ring of fork flutes 2, in each of which there is housed, for a certain angle of rotation of drum 1, a filter rod F supplied by a corresponding making machine (not shown). Filter rod F is held in respective fork flute 2 by suction exerted through the ducts 3.

During the time it is positioned on drum 1 and in the area of the respective angle of rotation of drum 1, each filter rod F is subjected to the testing of its air permeability. For this purposes, the drum has two side flanges 4 and 5 of which flange 4 slides on a fixed outer counter-flange 6. Provided in flange 4 there is a ring of perforated mouths 8, each coaxial to a filter rod F. In the other flange 5, plungers 9 are slidably mounted, each coaxial to a filter rod F and integral with a rod 10 which has a head 11 provied with a perforated mouth facing the filter rod. Each plunger 9 is urged by a spring 12 which tends to move head 11 away from filter rod F, while it keeps a stem 13 of plunger 9, provided with roller 14, engaged with a fixed cam 15 carried by a stationary part 7 of the device. The perforated mouth of each head 11 is connected by means of a flexible pipe 16 to a calibrated passage hole 17, which is provided in flange 5 of drum 1 and opens into the atmosphere.

Figure 1:
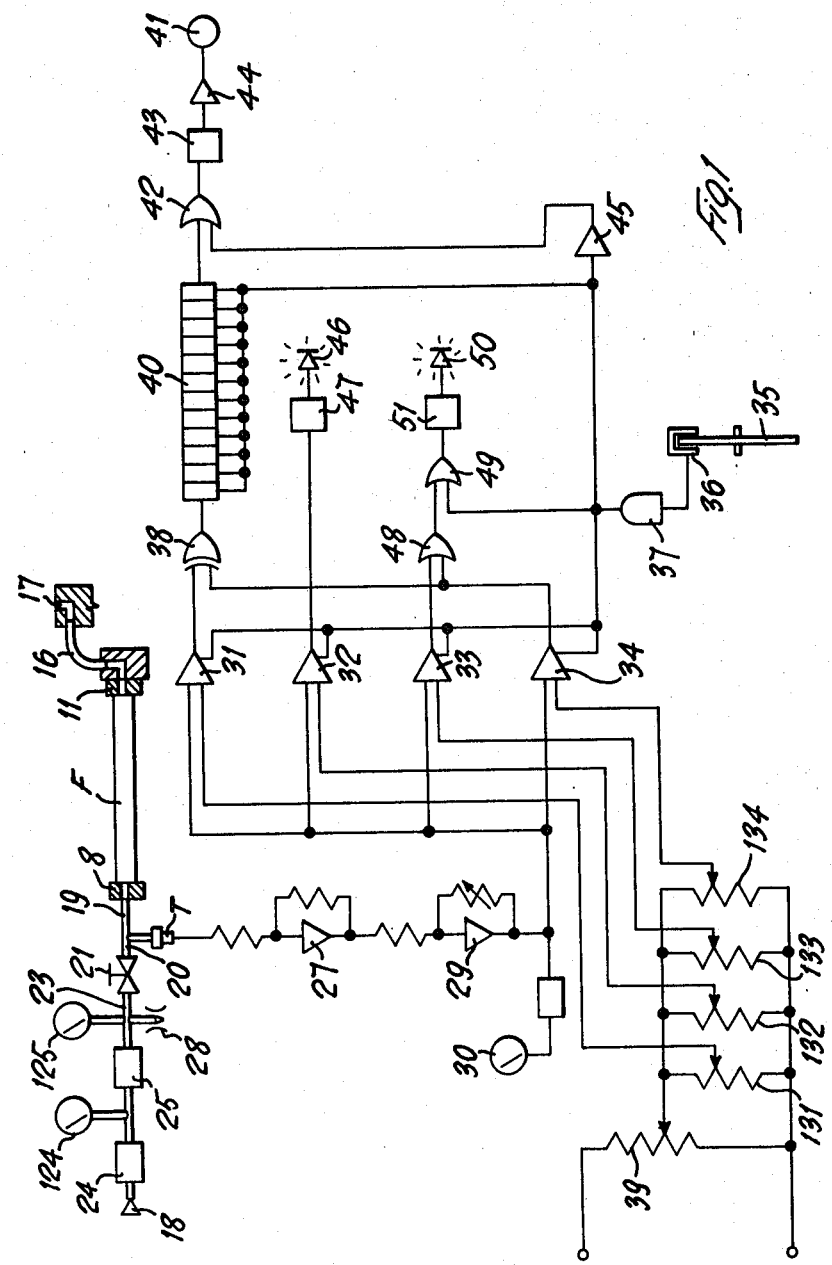
FIG. 1 shows the electric diagram of a device according to the invention.

When a filter rod F moves into a flute 2 of drum 1, plunger 9 is in a position in which head 11 is retracted outwardly with respect to rod F, that is towards flange 5, as shown in the lower part of FIG. 2. Subsequently, during the rotation of drum 1, plunger 9 is pushed inwardly by cam 15 against the action of spring 12, that is towards filter rod F, and moves the latter axially into the respective flute 2, until it adheres with its end, in air-tight manner, against the corresponding fixed mouth 8 in flange 4, while it compresses head 11 with the respective mouth in air-tight manner against the opposite end of filter rod F, as shown in FIGS. 1 and 2.

Under these conditions, while drum 1 continues to rotate, filter rod F is brought to an inspection or testing station, in which mouth 8 associated with an end of filter rod F is caused to communicate, by means of ducts and chambers provided in fixed outer counter flange 6 and indicated generally by 19, as well as by means of a tube 20 and an adjustable pressure reducing valve 21 provided in a fixed sector 22, with a duct 23 connected with a pneumatic pressure source. In the embodiment shown, the pneumatic pressure is obtained from a normal compressed air distribution network by means of a filter 18 whose purpose is to eliminate possible oil traces in the compressed air. The pressure is then reduced to the testing value and stabilized by means of two pressure regulators 24, 25 connected in series with each other and to successive pressure gauges 124 and 125. The second pressure regulator 25 has a continuous fixed basic consumption obtained by means of a calibrated loss 28. The pressure supplied by this second regulator, measured by means of gauge 125, is applied to filter rod F by means of tube 23 and of a known pneumatic reference resistance, consisting of a choke valve 21 which may be adjusted at will by the operator. Choke valve 21 consists of a conical needle valve, adjustable by means of a screw 26.

During the testing, the other end of filter rod F remains connected with the atmosphere by means of calibrated hole 17, through which a constant air flow passes.

The pneumatic pressure which is established at the inlet of filter rod F is characteristic for the permeability to the air of filter rod F and is converted by means of a pressure transducer T into an electric testing signal which can be used in any suitable circuit for deciding whether the inspected filter rod can be accepted or must be rejected. An embodiment of a circuit of this type is shown in FIG. 1, from which it evidently appears that the electric output signal of transducer T is applied, by means of a fixed gain amplifier 27 and of a successive variable gain amplifier 29, to provide an output value indicated by a peak voltmeter 30 averaged on a preset number of consecutive filter rods, simultaneously to four comparator circuits 31, 32, 33 and 34 which compare the level of the test signal with four respective thresholds, two of which are reject and two are alarm thresholds. The two reject thresholds, one higher and the other lower, are associated with comparators 31 and 34 and are determined individually and independently of each other, by means of potentiometers 131 and 134. The two alarm thresholds, one higher and the other lower, are within the band defined by the two reject thresholds and are closest to the desired value of the permeability of the air of the filter rods, defining a band narrower than that of the reject thresholds. The higher alarm threshold is associated with comparator 32, while the lower alarm threshold is associated with comparator 33. Also the two alarm thresholds are determined and adjusted individually and independently of each other by means of potentiometers 132 and 133. Furthermore, the four thresholds can be simultaneously changed and adjusted by means of a supply potentiometer 39.

Comparator circuits 31, 32, 33 and 34 are preferably inserted by means of a synchronizing signal obtained with the aid of a synchronizing disk 35 which rotates integrally with drum 1 and—in the embodiment shown—has a ring of through holes, whose number and whose angular distribution correspond to those of flutes 2 for accommodating filter rods F on drum 1. Located astride the perforated portion of synchronizing disk 35, there is a fixed U-shaped supporting element, an arm of which has a lamp and the other a photoelectric cell 36. The light which passes through the holes of rotary synchronizing disk 35 generates in photoelectric cell 36 synchronizing signals which are applied, by means of a Schmitt Trigger shaping circuit 37, to comparator circuits 33 and 34 in order to insert them in synchronism with the movement of filter rods F through the inspection station. As an alternative, comparator circuits 31, 32, 33, 34 can be permanently inserted. The electric signals at the output of the pair of comparators 31, 34 associated with the reject thresholds are sent to a logic circuit 38 of the EXCLUSIVE OR type, whose output is connected to a transfer memory 40 of the Shift Register type. The information stored in memory 40 moves sequentially from a first stage to the following stages in synchronism with the movement of the respective inspected filter rod. For this purpose transfer memory 40 is controlled, by means of Schmitt Trigger shaping circuit 37, by the synchronizing signals supplied by photoelectric cel 36 associated with disk 35.

The content of memory 40 is read when the respective inspected filter rod is in the area of the rejecting device which may be of any type and may be controlled for instance, by a solenoid valve 41. The output of memory 40 is connected to the input of an OR circuit 42 which controls, by means of a timer 43 and an amplifier 44, solenoid valve 41 of the rejecting device, by opening, for instance, the said valve when the signal supplied by memory 40 is in phase with one of the holes of disk 35. Timer 43 is provided for interrupting the operation of solenoid valve 41 in case the device stops with a reject signal present and in phase with one of the holes of disk 35. OR circuit 42 allows the rejection synchronization, because it receives a synchronizing signal from the output of Schmitt Trigger shaping circuit 37, by means of an inverting amplifier 45.

The output of comparator 32 relating to the higher alarm threshold is sent to an indicator, for instance, to a LED diode indicator 46, by means of a ONE-SHOT (monostable) circuit 47 so calibrated as to generate a light impulse whose duration is equal to that of a filter rod production at normal operation speed even if the duration of the alarm signal is very short. The output of comparator 33 relating to the lower alarm threshold and the output of comparator 34 relating to the lower reject threshold are applied to the two inputs of a NAND circuit 48. The output of this NAND circuit 48 and the synchronizing signals supplied by photoelectric cell 36 associated with disk 35 are applied to the two inputs of another NAND circuit 49, whose output is connected to a LED diode indicator 50 by means of a ONE-SHOT circuit 51, also preferably so calibrated as to generate a light impulse whose duration is equal to that of a filter rod production at normal operation speed. When the inspection signal relating to a filter rod exceeds the higher alarm threshold, but is still lower than the higher reject threshold, LED 46 illuminates, thus informing the operator that the permeability to the air of the inspected filter rod is getting close to the higher reject value. When, on the other hand, the inspection signal exceeds the lower reject threshold, but does not still reach the lower alarm threshold, LED 50 illuminates, thus informing the operator that the permeability of the produced filter rods is getting close to the lower reject threshold. In both cases, the operator may intervene on the filter rod making machine to decrease or increase the permeability to the air of the produced filter rods, in order to avoid rejections.

According to the invention, the electric alarm signals supplied by comparators 32, 33, instead of illuminating LEDs 46, 50 or of actuating other indicators, or besides illuminating LEDs or actuating other indicators, are used to control the filter rod making machine in order to automatically correct the air permeability of the produced filter rods. For this purpose, the alarm signals can control, for instance, the devices for stretching the filtering material, on which the longitudinal filter rod permeability depends. In this manner, a retroaction system is established between the filter rod maker and the device for detecting the permeability to the air of these rods. This retroaction system allows the maker to be automatically adjusted in such a way as to produce filter rods with a permeability to the air included between those corresponding to the two alarm thresholds.

In order to accurately calibrate the alarm thresholds, the reject comparator circuits 31, 34 and alarm comparator circuits 32, 33 can be switched between each other. In this manner, it is possible to reject and then examine individually the filter rods which exceed the higher alarm threshold or do not reach the lower alarm threshold. For this purose, the outputs of the two reject comparators 31, 34 are simply to the outputs of the two alarm comparators.

It is understood that the invention is not restricted to the embodiments which have been described and illustrated but may be broadly changed and modified, mainly from a constructive viewpoint. Thus, for instance, the testing signal supplied by transducer T, instead of being applied to comparator circuits, can be converted into a digital signal and applied to an appropriate electronic computer which determines the rejection of the filter rods and emits warning signals and/or controls the device, regulating the air permeability of the filter rods in the respective making machine.

I claim:

1. A method of determining the permeability to the air of filter rods for filter tip cigarettes, comprising the steps of:
    applying a fluid under pneumatic pressure to one end of a filter rod, the other end of said filter rod being connected to the atmosphere through a calibrated passage;
    converting the pneumatic pressure at said one end of said filter rod to an inspection signal corresponding to the permeability of said filter rod;
    generating higher and lower reject threshold signals, the value of said higher reject threshold signal corresponding to a permeability of said filter rod which exceeds an upper permissible limit and the value of said lower reject threshold signal corresponding to a permeability of said filter rod which is less than a lower permissible limit;
    generating higher and lower alarm threshold signals having values between those of said higher and lower reject threshold signals;
    comparing said inspection signal with said reject and alarm threshold signals;
    generating an alarm signal when said inspection signal exceeds said higher alarm threshold signal or is less than said lower alarm threshold signal; and
    generating a reject signal when said inspection signal exceeds said higher reject threshold signal or is less than said lower reject threshold signal.

2. The method defined by claim 1 which comprises the further step of coupling said alarm signal to a device for controlling the permeability of said filter rod, said device automatically adjusting the permeability of said filter rod during manufacture thereof.

3. Apparatus for determining the permeability to the air of filter rods for filter tip cigarettes, comprising
    means for applying fluid at a pneumatic pressure to one end of a filter rod and for connecting the other end of said filter rod to the atmosphere through a calibrated passage;
    a transducer for converting the pneumatic pressure at said one end of said filter rod to an inspection signal corresponding to the permeability of said filter rod;
    higher and lower reject threshold generating means, the output signal of said higher reject threshold generating means corresponding to a permeability of said filter rod which exceeds an upper permissible limit and the output signal of said lower reject threshold generating means corresponding to a permeability which is less than a lower permissible limit;
    higher and lower alarm threshold generating means, the output signals of said higher and lower alarm threshold generating means having values between those of said higher and lower reject threshold generating means corresponding to permeabilities of said cigarettes between said upper and lower permissible limits;
    comparison means coupled to said transducer and said reject and alarm threshold generating means for comparing said inspection signal with the output signals of said reject and alarm threshold generating means;
    alarm signal generating means coupled to the output of said comparison means for generating an alarm signal when said inspection signal exceeds the output signal of said higher alarm threshold generating means or is less than the output signal of said lower alarm threshold generating means; and
    reject signal generating means coupled to the output of said comparison means for generating a reject signal when said inspection signal exceeds the output signal of said higher reject threshold generating means or is less than the output signal of said lower reject threshold generating means.

4. Apparatus as defined by claim 3 which further comprises a device for controlling the permeability of said filter rod during manufacture, said device being coupled to the output of said alarm signal generating means.

5. Apparatus as defined by claim 3 wherein said means for applying a pneumatic pressure to one end of said filter rod comprises a variable pneumatic resistance, said pneumatic resistance including a filter, pressure reducing and stabilizing elements and an adjustable choke valve.

6. Apparatus as defined by claim 5 wherein said pressure reducing and stabilizing elements comprise first and second series-connected pressure reduction units, said second unit having a fixed basic consumption consisting of a calibrated loss.

7. Apparatus as defined by claim 3 wherein said comparison means comprises first, second, third and fourth comparator circuits each having a first input coupled to the output of said transducer, said first, second, third and fourth comparator circuit each having in addition a second input coupled to said higher reject threshold generating means, said higher alarm threshold generating means, said lower alarm threshold generating means and said lower reject threshold generating means, respectively; a transfer memory; an exclusive OR circuit coupling the outputs of said first and fourth comparator circuits to the input of said memory device; a timer coupling the output of said memory device to said reject signal generating means; and synchronizing signal generating means coupled to said comparator circuits, transfer memory and timer for control thereof in accordance with the rate at which said filter rods pass through said apparatus.

8. A pparatus as defined by claim 7 which further comprises a first indicating device coupled to the output of said second comparator; a first NAND circuit having first and second inputs coupled to the outputs of said third and fourth comparators, respectively; a second NAND circuit having a first input coupled to the output of said first NAND circuit and a second input coupled to the output of said synchronizing signal generating means; and a second indicating device coupled to the output of said second NAND circuit.

9. Apparatus as defined by claim 8 wherein said transfer memory comprises a shift register and said first and second indicating devices are light-emitting diodes.

10. Apparatus as defined by claim 8 which further comprises a first ONE-SHOT circuit coupled between the output of said second comparator and said first indicating device and a second ONE-SHOT circuit coupled between the output of said second NAND circuit and said second indicating device, said first and second ONE-SHOT circuits being calibrated to provide light pulses from said first and second indicating devices having a duration equal to that of the normal rate at which said filter rods pass through said apparatus.

11. Apparatus as defined by claim 7 which further comprises means for adjusting simultaneously all of said threshold generating means, each of said threshold generating means also being individually adjustable.

12. Apparatus as defined by claim 7 which further comprises series-connected fixed gain and variable gain amplifiers coupled between said transducer and the first inputs of each of said comparator circuits.

13. Apparatus as defined by claim 7 wherein means are provided for switching the outputs of said first and fourth comparators with the outputs of said second and third comparators, said switching means permitting the rejection and individual examination of filter rods having permeabilities which exceed the higher alarm threshold or do not reach the lower alarm threshold.

14. Apparatus as defined by claim 3 which further comprises a device for controlling the permeability of said filter rod during manufacture, said device being coupled to the outputs of said second and third comparator circuits.

* * * * *